(12) United States Patent
Wagner et al.

(10) Patent No.: US 6,911,249 B2
(45) Date of Patent: Jun. 28, 2005

(54) SURFACE FOR USE ON IMPLANTABLE DEVICE

(75) Inventors: Donald J. Wagner, Venetia, PA (US); Donald J. Wagner, II, Bridgeville, PA (US); Rodney Bristol, Round Rock, TX (US)

(73) Assignee: MedSource Technologies Pittsburgh, Inc., Houston, PA (US)

( * ) Notice: Subject to any disclaimer, the term of this patent is extended or adjusted under 35 U.S.C. 154(b) by 73 days.

(21) Appl. No.: 10/339,816

(22) Filed: Jan. 10, 2003

(65) Prior Publication Data

US 2004/0134886 A1 Jul. 15, 2004

(51) Int. Cl.[7] ............................. B32B 3/30; D06N 7/04
(52) U.S. Cl. ........................... 428/141; 216/11; 216/41
(58) Field of Search ................................ 428/141, 156; 216/34, 41, 52

(56) References Cited

U.S. PATENT DOCUMENTS

| | | | |
|---|---|---|---|
| 4,818,572 A | | 4/1989 | Shimamune et al. ........ 427/327 |
| 5,258,098 A | | 11/1993 | Wagner et al. ............... 216/52 |
| 5,411,629 A | * | 5/1995 | Warfield ..................... 216/34 |
| 5,507,815 A | | 4/1996 | Wagner et al. ............... 623/16 |
| 5,639,536 A | * | 6/1997 | Yamazaki et al. ........... 428/141 |
| 5,705,082 A | * | 1/1998 | Hinson ........................ 216/95 |
| 5,922,029 A | | 7/1999 | Wagner et al. ............... 623/66 |
| 6,193,762 B1 | | 2/2001 | Wagner et al. ............... 623/66 |

FOREIGN PATENT DOCUMENTS

EP  0947 605 A1 * 10/1999

* cited by examiner

Primary Examiner—Shamim Ahmed
(74) Attorney, Agent, or Firm—Metz Lewis LLC; Barry I. Friedman

(57) ABSTRACT

An attachment surface for an implantable device has an irregular pattern formed through a process including masking, chemical or electrochemical etching, blasting and debris removal steps. Surface material is removed from the implant surface without stress on the adjoining material and the process provides fully dimensional fillet radii at the base of the surface irregularities. This irregular surface is adapted to receive the ingrowth of bone material and to provide a strong anchor for that bone material which is resistant to cracking or breaking. The surface is prepared through an etching process which utilizes the random application of a maskant and subsequent etching in areas unprotected by the maskant. This chemical etching process is repeated a number of times as necessitated by the nature of the irregularities required in the surface. The blasting and debris removal steps produce microfeatures on the surface that enhance the ingrowth of bone material.

31 Claims, 7 Drawing Sheets

SURFACE FOR USE ON IMPLANTABLE DEVICE

BACKGROUND OF THE INVENTION

1. Field of the Invention

The present invention relates to an improved irregular surface which may be utilized in conjunction with a bone implant to facilitate the growth of bone tissue within the surface. The invention also relates to a method of production of this surface. The irregular surface is created on a substrate material to particularly adapt that surface for joining to a second material. More specifically, the invention relates to the sequential etching of a bone implant surface to produce an irregular random pattern of protrusions and depressions through the use of chemical and electrochemical milling techniques and the subsequent blasting of the surface to produce micro features on the surface.

2. Description of the Prior Art

In the field of bone implantation, or the use of man-made objects to replace portions of bone within the human body, there are two primary methods of affixing the implant device to the existing bone. The first of these methods involves the use of a cement or adhesive material which is applied to the surfaces of the implant and the bone. The cement is adapted to harden in a rapid fashion and rigidly affix the two portions in an immobile manner. The use of cement permits the application of loads to the joinder of the bone and the implant within a relatively short time following implantation. This is generally desirable in terms of the well-being of the patient, in that a quick physical recovery improves the overall recovery of the patient.

One of the significant shortcomings of a cement adhesion of the two elements is that over time, the cement tends to deteriorate. This deterioration may permit relative movement between the implant and the bone surface and if untreated, could allow the two joined elements to separate. In either event, the result is painful and dangerous to the patient.

A second method of affixation of the implant to the bone has also been utilized as an alternative to the cement technique. In this embodiment, the implant is provided with an irregular surface into which the bone may grow, creating a natural joinder between the bone and the implant. One of the shortcomings of this implantation technique, however, is the longer recovery time necessary to permit ingrowth of the bone into the surface of the implant. An additional problem which has occurred with relation to the ingrowth embodiment relates to the preparation of the surface of the implant. An implant having a smooth surface is inappropriate for use in this type of operation as it provides no gripping surface for the bone. An irregular surface, therefore, is preferred and in fact necessary for this application. Several methods have been proposed in the prior art for the preparation of the surface, such that a stable gripping surface will be provided into which the bone may grow.

Frye, U.S. Pat. No. 4,272,855, issued Jun. 16, 1981, discloses the use of generally conical projections emanating from the surface of the implant. These projections may be perpendicular to the surface of the implant or may be extending outwardly at an angle between 50.degree. and 90.degree., with respect to the surface of the implant Frye teaches that an increase in the anchoring surface is a decisive feature which can influence and improve the bond between tissue and the implant. The projections described in Frye are generally regular in shape and devoid of comers and edges and have transition surfaces merging into the base level.

Van Kampen, U.S. Pat. No. 4,673,409, issued Jun. 16, 1987, discloses an implant having a surface comprising a multiplicity of spaced posts projecting from the implant surface for mating with bone material. The Van Kampen reference specifically teaches away from an edgeless surface as taught by the Frye reference. Van Kampen instructs that while a rounded surface minimizes the formation of stresses, it minimizes the total surface area that may be joined to the tissue, thus reducing the strength of the implant. Van Kampen discloses the use of regular posts which are roughly rectangular in cross-section. The posts are spaced at a regular interval and are formed by laser drilling.

It is evident from the teaching of these two references that there is some disagreement in the art regarding the best approach towards the preparation of an implant surface.

Another technique in the preparation of an implant surface is disclosed in Sump, U.S. Pat. No. 4,644,942, issued Feb. 24, 1987. The Sump reference discloses the use of a coating which is applied to the surface of the implant. The coating is comprised of a solid metallic powder and a solution of organic binders. A slurry formed of the two elements is applied to the surface of the implant and is permanently affixed thereto under controlled temperature and pressure conditions. The organic material is subsequently removed, leaving a porous, metallic coating on the surface of the implant.

Other techniques for applying a similar coating include plasma spray of a metallic material onto the surface of an implant resulting in a similar metallic irregular coating. While these porous coatings do provide an attachment surface into which bone may grow, these surfaces and the surface described in Noiles, U.S. Pat. No. 4,865,603, issued Sep. 13, 1989, exhibit significant shortcomings. The Noiles reference describes a surface in which furrows and depressions are cut or stamped into the surface of the implant. Each of these surfaces involves the addition of metallic material or the manipulation of the metallic surface of the implant. Each of these methodologies provides a surface that is subject to breakage and dislocation under stress. A metallic addition to the surface of the implant, even under rigorously controlled conditions, forms a joinder which is more easily broken than a singularly formed piece of metallic substrate. Similarly, the manipulation of the surface of the implant, even though formed of a single integral metal substrate, involves the stressing of the metallic surface which forms a locus for breakage when the implant is under a load.

In Wagner et al., U.S. Pat. Nos. 5,507,815 and 5,258,098, an attachment surface is provided in which a random irregular pattern is formed through a repetitive masking and chemical milling process. Surface material is removed from the implant without stress on the adjoining material, and the process provides fully dimensioned fillet radii at the base of the surface irregularities which is then adapted to receive the ingrowth of bone material when joined to bone during implantation. An irregular series of projections and depressions is formed to accommodate such ingrowth, providing a large surface area without any surface manipulations or additions.

The surface is prepared through an etching process which utilizes the random application of a maskant and subsequent etching of the metallic substrate in areas unprotected by the maskant. This etching process is repeated a number of times as necessitated by the amount and nature of the irregularities required for any particular application. The number of repetitions of the etching process is also utilized to control the surface features.

Cobalt-chromium alloys present a particular challenge for material removal utilizing this technique, primarily because of their high chemical inertness which makes them resistant to chemical etching. Wagner, et al., U.S. Pat. Nos. 5,922,029 and 6,193,762 disclose the preparation of a substrate through an electrochemical etching process which utilizes the random application of a maskant and subsequent electrochemical etching of the metallic substrate in areas unprotected by the maskant. This electrochemical etching process is repeated a number of times as necessitated by the amount and nature of the irregularities required for any particular application.

SUMMARY OF THE INVENTION

An attachment surface is provided in which a random irregular pattern is formed through a repetitive masking and chemical milling process. In some applications, such as the affixation of a composite material to a rigid or metallic substrate, the malleable composite material is molded into the irregularities of the substrate. As utilized in the production of some aircraft components, for example, a malleable, composite surface material is deposited upon a metal superstructure, which provides strength and support. The composite outer layer is designed to provide external characteristics, such as reduced air resistance or increased absorbability of electromagnetic radiation. When the substrate is a bone implant adapted to use in the human body, surface material is removed from the implant without stress on the adjoining material, and the process provides fully dimensioned fillet radii at the base of the surface irregularities which is then adapted to receive the ingrowth of bone material when joined to bone during implantation. An irregular series of projections and depressions is formed to accommodate such ingrowth, providing a large surface area without any surface manipulations or additions.

Where the invention employs chemical etching, control of the strength of the etchant material, the temperature at which the etching process takes place and the time allotted for such an etching technique permit fine control over the resulting surface produced by the process. The number of repetitions of the etching process is also utilized to control the surface features.

The particular maskant and etchant utilized for a given attachment surface is dictated by the base metal utilized for the implant while a titanium implant is contemplated as the best mode of practice in the invention, it is to be specifically understood that any base metal may be utilized as the implanted material. A change in the base metal would necessitate a change in the maskant and etchant. No limitation is to be inferred from the selection of titanium in the detailed description following nor in the selection of the particular maskant and etchant chemistries.

The surface of cobalt-chromium alloys are preferably prepared through an electrochemical etching process which utilizes the random application of a maskant and subsequent electrochemical etching of the metallic substrate in areas unprotected by the maskant. Control of the composition, temperature, and flow rate of the electrolyte, the work gap between the cathodic tool and the attachment surface of the anodic workpiece, the voltage difference between the cathodic tool and the anodic workpiece, the specific amperage, the temperature at which the electrochemical etching process takes place, and the time allotted for electrochemical etching permit fine control over the resulting surface produced by the process. The number of repetitions of the electrochemical etching process is also utilized to control the surface features.

The particular maskant and the parameters of the electrochemical etching process utilized for a given attachment surface is dictated by the base metal utilized for the implant. While a cobalt-chromium allow implant is contemplated as the best mode of practice in the invention, it is to be specifically understood that any base metal may be utilized as the implanted material. A change in the base metal may necessitate a change in the maskant, the electrolyte, and the parameters of the electrochemical etching process. No limitation is to be inferred from the selection of a cobalt-chromium allow in the detailed description which follows no in the selection of the particular maskant and of the particular parameters of the electrochemical etching process.

A final procedure provides the substrate with an enhanced surface texture having a plurality of micro-features that promote bone ingrowth or osseointegration. After completion of the initial masking and etching steps, the resulting surface is subjected to a blasting step in which a blast media is impinged upon the surface. One or more of the following five variables will, depending on the type of equipment being used, affect the surface texture produced and that must be taken into consideration during this blasting step: (1) the particular blast media chosen and the grit size thereof; (2) the duration of the blast; (3) the pressure of the blast stream; (4) the distance between the source of the blast media, such as a nozzle, and the surface being treated; and (5) the angle at which the source of the blast media, and thus the stream of the blast media, is directed toward the surface being treated. The blast media is selected according to the particular parameters of each application, depending upon the size and characteristic micro-features desired. The blast media is also selected in conjunction with a matched solvent that can dissolve or otherwise remove, without damage to the substrate material, any blast media material which is lodged into the substrate after blasting.

After the blasting step, the surface may be subjected to an optional cold flash step to remove stains in which the surface is immersed in a solvent or other bath for the purpose of cleaning the surface and removing any stains. Any special areas of the surface, such as threaded holes or trunnions, may be plugged or covered to prevent damage thereto.

The embedded particulate debris from the blast media is removed during a debris removal step. The debris removal step preferably follows the cold flash step, in which the surface is immersed in a solvent bath that leaches the embedded blast media particulate debris from the surface.

Performing the blasting and debris removal or passivation steps according to the present invention on the surface will result in a surface that includes a plurality of micro-features comprising recesses or indents that promote greater osseointegration.

These and other advantages and features of the present invention will be more fully understood upon reference to the presently preferred embodiments thereof and to the appended drawings.

DESCRIPTION OF THE PREFERRED EMBODIMENTS

Figure 1:
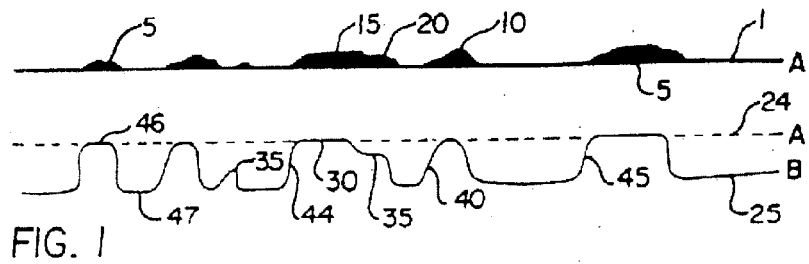
FIG. 1 is a diagrammatic representation of a first cycle of the etching process, illustrating a first surface having a maskant applied thereto and a second surface indicating the resultant surface after etching.

A. Chemical Etching Embodiments:

In describing the preferred embodiment of the invention when chemical etching is employed and the best mode of carrying the invention out, the drawings and description refer to the use of a titanium alloy base metal. While titanium is the preferred embodiment for the implantable material, a number of other alloys may be utilized. Each of these different alloys will require a different maskant and etchant composition. Other than cobalt chromium, no specific details are given in the specification regarding the use of these other metals and etchants. It is, however, considered to be well within the knowledge of an experienced practitioner in the art to select an etchant once a base alloy has been identified. Furthermore, for the purposes of clarity, certain repetitive elements in the drawings have not been numerically identified for each and every occurrence. For example, a number of maskant points are shown on the surface diagrams. It is considered apparent from the drawings that the maskant points and other surface features of the etched implant are repeated and are readily identifiable without the aid of numeric identification for each feature. Only representative features and maskant points have therefore been identified.

Referring now to FIG. 1, an unfinished surface 1 is provided which diagrammatically represents the exterior surface of the device to be implanted. The letter identifiers on the right margin of the drawings are intended to provide a quick reference to the relative levels of etching. Unfinished surface 1 at level A is generally smooth and comprised of titanium metal or alloy such as Ti—6Al—4Va. As stated herein, a cobalt chromium alloy is also contemplated. A maskant is applied to the surface of the implant which is to be etched in a random fashion. Several methods may be utilized to accomplish the random spattering of the maskant on the surface. Among these are manually applying the maskant by brushing it using the tips of a hair-type brush or utilizing any type of shredded hair-like fibrous applicator dipped in the maskant material. Another method of application would be delivered in an air stream utilizing an air brush or paint gun.

The maskant must be chosen carefully in order to provide a substance which will cling tightly to the surface of the implant during manipulation of the implant and will also remain stable when the etchant solution is applied to the coated part. The maskant must also be removed with no residue once its function has been accomplished A particular problem encountered when utilizing maskants is the performance of the maskant at the boundaries of its application. The maskant should produce a sharply defined edge once the etching process has begun and not itself deteriorate during the etching process. This might permit partial degradation of the substrate in a masked area It should be noted, however, that some deterioration is found in any maskant use and does provide some of the particular surface features of the etched implant described later.

The surface 1 of the implant must be clean and grease-free and any oxidized material should be removed before the application of the maskant. This may be accomplished either mechanically, chemically or both. The surface may be cleaned mechanically utilizing a light abrasive blast of aluminum oxide particles or glass beads. Alternatively, blasting with any small solid particle which will not degrade the surface is contemplated A chemical agent such as methanol may be utilized alone or in conjunction with the blasting. Most maskants are very sensitive to the condition of the applied surface and both application and removal of the maskant may be affected by improper surface treatment. The maskant can be comprised of a number of materials including neoprene elastomers and isobutylene isoprene copolymers. The particular maskant should be selected based on the type of etchant utilized. The preferred maskant is AC-818C, an air-cured, general purpose, peelable coating produced by A.C. Products, Inc. of Placentia, Calif. The maskant is thinned utilizing perchlorethylene to 35–45 seconds utilizing a No. 5 Zahn cup. The maskant, if too thin, may be thickened to this viscosity by evaporation of the carrier. While the maskant is traditionally utilized in the 14–18 second range, it has been found that this thicker version produces superior results in terms of applying the maskant utilizing manual daubing or spray application techniques. It is to be specifically noted that the maskant is applied in a random spattered fashion allowing only a portion of the surface of the implant to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80–120 mesh grit at 80–90 psi. to assist in providing an irregular maskant coating.

As shown in FIG. 1, a variety of applied maskant points 5 are illustrated. A particularly thick maskant agglomeration 10 is also illustrated. Other surface features of the applied maskant include an applied maskant plateau 15 and an applied maskant thin layer 20. It is desirable to achieve a variety of sizes and thicknesses of maskant in order to obtain the proper random finished surface. As will be seen later, each of these particular maskant surface features produces a somewhat different etched result. An optional step of drying the maskant at an elevated temperature is also contemplated. Four to five minutes at 200.degree. F. is sufficient.

Referring now to the second illustration of FIG. 1, the etched result is illustrated, based on the applied maskant shown in the upper illustration. The unfinished surface indication line 24, shown as a chain, indicates the original level identified by the letter A at which the surface began. The first etched surface 25 identified by the letter B shows the resultant etched surface. While a number of etchants could be utilized, the particular chemistry adopted for the preferred embodiment utilizes a standard 30% nitric acid—6% hydrofluoric acid combination which is commonly marketed and well known in the art. The etchant is applied at 110.degree. F. for approximately 4 minutes to achieve a desired 0.008–0.010 inch etch depth. This time period or the strength of the etchant solution may be adjusted upwardly or downwardly to achieve a heavier or lighter etching. The etching is halted in a water bath or spray.

The maskant material may be removed in a variety of ways. The material may be removed mechanically or chemically. Depending on the size and number of coated objects, mechanical brushing or blasting of the maskant will peel it off. Additionally, the use of nitric acid is contemplated to dissolve the maskant material.

Referring again to the second illustration of FIG. 1, a number of surface features may be identified. A primary plateau 30 corresponds to the applied maskant plateau 15 illustrated in the top drawing. The heavy maskant coat completely protects the implant surface, preventing any metallic material from being removed at this point. A secondary plateau 35 corresponds to the thin layer 20 illustrated in the above drawing. The intermediate height of the secondary plateau between levels A and B indicates that the maskant performed for some period during the etching cycle but failed at an intermediate time allowing some of the alloy to be etched away. A small promontory, third from the left as shown in FIG. 1, also illustrates a small secondary plateau 35. Gradually sloped feature 40 corresponds to a gradually tapering maskant coverage which partially protects the underlying substrate during the etching cycle. A highly sloped feature 44 indicates a thicker maskant coating which enjoyed a highly defined perimeter before etching. A medium sloped feature 45 indicates a maskant condition intermediate the two previously described. The extremes of the etching are indicated by unetched level 46 and first etched level 47 which illustrate the effect of complete maskant coating versus no maskant coating. It should be noted that the base of each surface feature provides full dimensionally filleted radii.

Figure 2:
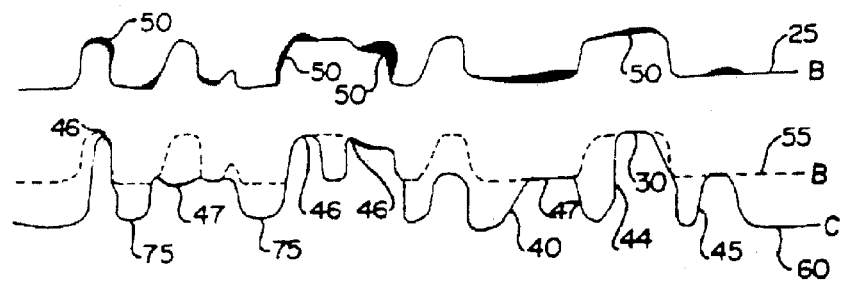
FIG. 2 is a diagrammatic representation of the second cycle of the etching process, illustrating the second surface illustrated in FIG. 1 having a maskant applied thereto and a resultant third surface prepared by etching the masked second surface.

FIG. 2 also employs two illustrations to display the effects of a second masking/etching cycle. The upper illustration corresponds to the second illustration of FIG. 1, the lowest extreme being found at the level indicated as B. The maskant is again applied to a clean and prepared surface in a random fashion according to the same techniques described with reference to FIG. 1. As before, a randomized pattern is preferable in which a wide variety of maskant surface features is achieved. Second applied maskant points 50 illustrate a variety of positions in which the maskant may be applied to the now irregular surface features of first etched surface 25.

Moving to the second illustration of FIG. 2, the first etched surface indication line 55 is shown in chain line to indicate the previous surface prior to the second etching cycle. The second etching cycle is performed under identical conditions as that described with reference to FIG. 1 to again achieve a 0.008–0.010 inch maximum etch. Second etched surface 60 is shown at level C, indicating a resultant etched surface. As previous described, the number of surface features are illustrated corresponding to the characteristics of the applied maskant. A highly sloped surface feature 44 corresponds again to a sharply defined and relatively thick application of maskant while a gradually sloped surface feature 40 corresponds to a gradually thinning maskant application. This feature is particularly visible in the two illustrations contained in FIG. 2 in which the gradual thinning of the maskant application is particularly exaggerated.

As can be seen in the second illustration of FIG. 2, three major levels of surface features are illustrated with a few intermediate features present to demonstrate the effects of partial maskant failure. A few points remain at unetched level 46 indicating maskant coverage during both etchant cycles. Some points are illustrated at first etched level 47 indicating maskant coverage during one of the two cycles, while points located at second etched level 75 have been exposed to the etchant during both of the etching cycles. The increasing level of complexity of surface forms is apparent with comparison between FIGS. 1 and 2.

Figure 3:
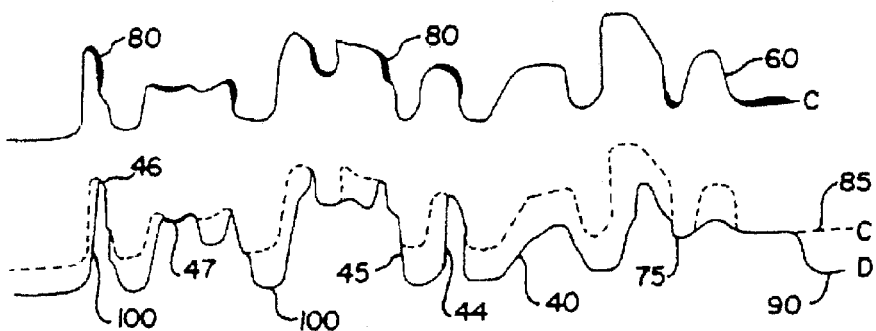
FIG. 3 is a diagrammatic representation of the third cycle of the etching process illustrating the resultant third etched surface of FIG. 2, also having a maskant applied thereto and a fourth surface prepared by etching the masked surface.

FIG. 3 is essentially a repetition of FIG. 2 having an upper illustration showing the application of third applied maskant points 80 to the now highly featured second etched surface 60 at level C. The increasing complexity of the surface of the etched device contributes also to the complexity of the maskant forms when applied to the irregular surface. The second illustration of FIG. 3 is shown to demonstrate the effect of a less rigorous etching cycle, being roughly one-half of the depth shown in FIGS. 1 and 2. The number and length of each etching cycle is purely dependent on the complexity of features required by the application and may be performed by any order. As shown in the second illustration of FIG. 3, a gradually sloped surface feature 40 retains its gradually sloped character from one cycle to the next when not covered by a maskant. This is to illustrate the consistent and uniform attack on the surface by the etchant solution. Highly sloped surface feature 44 again illustrates the effect of a highly stable maskant agglomeration while medium sloped surface feature 45 again demonstrates an intermediate condition. As illustrated in the second drawing of FIG. 3, four major surface levels are illustrated. Points at unetched level 46 are still apparent although fewer in number and relatively rare. A number of plateaus remain at first etched level 47 and second etched level 75. Those areas which have been exposed during all three etchant cycles enjoy depressions at third etched surface 100 corresponding to level D in FIG. 3. These levels correspond to areas which have had coverage during all three cycles, two cycles, one cycle and no cycles, respectively. The result as shown by third etched surface 90 is of a highly non-uniform featured surface which, compared with its length, also exhibits a large surface area. The different levels of depression and protrusion are particularly adapted to permit the ingrowth of bone and to allow for a firm anchoring of the bone along the surface of the implant structure.

Figure 4:
FIG. 4 is a photomicrograph of the chemically etched surface.

FIG. 4 illustrates a sample resultant surface. While specific identification of the surface features is difficult, a long ridge line is visible extending diagonally from upper left to lower right. A first level of three plateaus is visible at the center of the Figure, and lower level features extend outwardly in the upper right and lower left directions. All surface features are fully filleted and irregularly shaped to promote bone ingrowth.

B. Electrochemical Etching Embodiments:

In describing the preferred embodiment of the invention when electrochemical etching is employed and the best mode of carrying the invention out, the drawings and description refer to the use of a cobalt-chromium alloy base metal. While cobalt-chromium alloy is the preferred embodiment for the implantable material, a number of other alloys may be utilized in connection with electrochemical etching. Each of these different alloys may require a different maskant and electrochemical etching conditions. While no specific details are given in the specification regarding the use of these other metals and electrochemical etching conditions, it is considered to be well within the knowledge of an experienced practitioner in the art to select the appropriate electrochemical etching conditions once a base alloy has been identified. Furthermore, for the purposes of clarity, certain repetitive elements in the drawings have not been numerically identified for each and every occurrence. For example, a number of maskant points are shown on the surface diagrams. It is considered apparent from the drawings that the maskant points and other surface features of the etched implant are repeated and are readily identifiable without the aid of numeric identification for each feature. Only representative features and maskant points have therefore been identified.

Referring now to FIG. 1, an unfinished surface 1 is provided which diagrammatically represents the exterior surface of a device, such as a bone implant, that is to be joined to a second material. The letter identifiers on the right margin of the drawings are intended to provide a quick reference to the relative levels of electrochemical etching. Unfinished surface 1 at level A is generally smooth and comprised of cobalt-chromium alloy such as the cobalt-28 chromium-6 molybdenum alloy described in Table 1. A maskant is applied to the surface of the device which is to be electrochemically etched in a random fashion. Several methods may be utilized to accomplish the random spattering of the maskant on the surface. Among these are manually applying the maskant by brushing it using the tips of a hair-type brush or utilizing any type of shredded hair-like fibrous applicator dipped in the maskant material. Another method of application would be delivered in an air stream utilizing an air brush or paint gun.

TABLE I

| | Composition of Cobalt-28 minimum %* | Chromium-6 maximum %* | Molybdenum Alloy tolerance +/− %* |
|---|---|---|---|
| Chromium | 26.0 | 30.0 | 0.30 |
| Molybdenum | 5 | 7 | 0.15 |
| Nickel | — | 1.0 | 0.05 |
| Iron | — | 0.75 | 0.03 |
| Carbon | — | 0.35 | 0.02 |
| Silicon | — | 1.0 | 0.05 |
| Manganese | — | 1.0 | 0.03 |
| Nitrogen | — | 0.25 | 0.03 |
| Cobalt | balance | — | — |

*weight percent.

The maskant must be chosen carefully in order to provide a substance which will cling tightly to the surface of the device during manipulation of the device and will also remain stable when the etchant solution is applied to the coated part. The maskant must also be removed with no residue once its function has been accomplished. A particular problem encountered when utilizing maskants is the performance of the maskant at the boundaries of its application. The maskant should produce a sharply defined edge once the electrochemical etching process has begun and not itself deteriorate during the electrochemical etching process. This might permit partial degradation of the substrate in a masked area It should be noted, however, that some deterioration is found in any maskant use and does provide some of the particular surface features of the electrochemical etched device described later.

The surface 1 of the device must be clean and grease-free and any oxidized material should be removed before the application of the maskant This may be accomplished either mechanically, chemically or both. The surface may be cleaned mechanically utilizing a light abrasive blast of 80 to 120 grit aluminum oxide particles or glass beads. Alternatively, blasting with any small solid particle which will not degrade the surface is contemplated. All blasting residue is to be removed by brushing. A chemical agent such as acetone may be utilized alone or in conjunction with the blasting to clean the surface 1. Most maskants are very sensitive to the condition of the applied surface and both application and removal of the maskant may be affected by improper surface treatment.

The maskant can be comprised of a number of materials including neoprene elastomers and isobutylene isoprene copolymers. The preferred maskant for use with cobalt-chromium alloys is an alkaline soluble, air-curable phenol-formaldehyde resin maskant material such as Hysol ER1006 produced by The Dexter Corporation, Industry, Calif.

It is to be specifically noted that the maskant is applied in a random spattered fashion allowing only a portion of the surface of the device to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80–120 mesh grit at 80–90 psi to assist in providing an irregular maskant coating.

The viscosity of the maskant should be adjusted to a level that promotes both the application of the maskant in a random spattered panern and the proper curing of the maskant. The maskant may be thinned to the optimum viscosity by the addition of its carrier fluid. If the maskant is too thin, the maskant may be thickened to a lower viscosity by evaporation of its carrier fluid. For the Hysol ER1006 maskant, the optimum viscosity is about 60–66 seconds as measured utilizing a No. 5 Zahn cup.

After the maskant has been applied in a random spattered pattern, it is cured. For example, the Hysol ER1006 maskant is preferably cured for a minimum of about 20 minutes at between about 200–250.degree. F. and then air cooled to room temperature.

As shown in FIG. 1, a variety of applied maskant points 5 are illustrated. A particularly thick maskant agglomeration 10 is also illustrated. Other surface features of the applied maskant include an applied maskant plateau 15 and an applied maskant thin layer 20. It is desirable to achieve a variety of sizes and thicknesses of maskant in order to obtain the proper random finished surface. As will be seen later, each of these particular maskant surface features produces a somewhat different electrochemical etching result.

Figure 5:
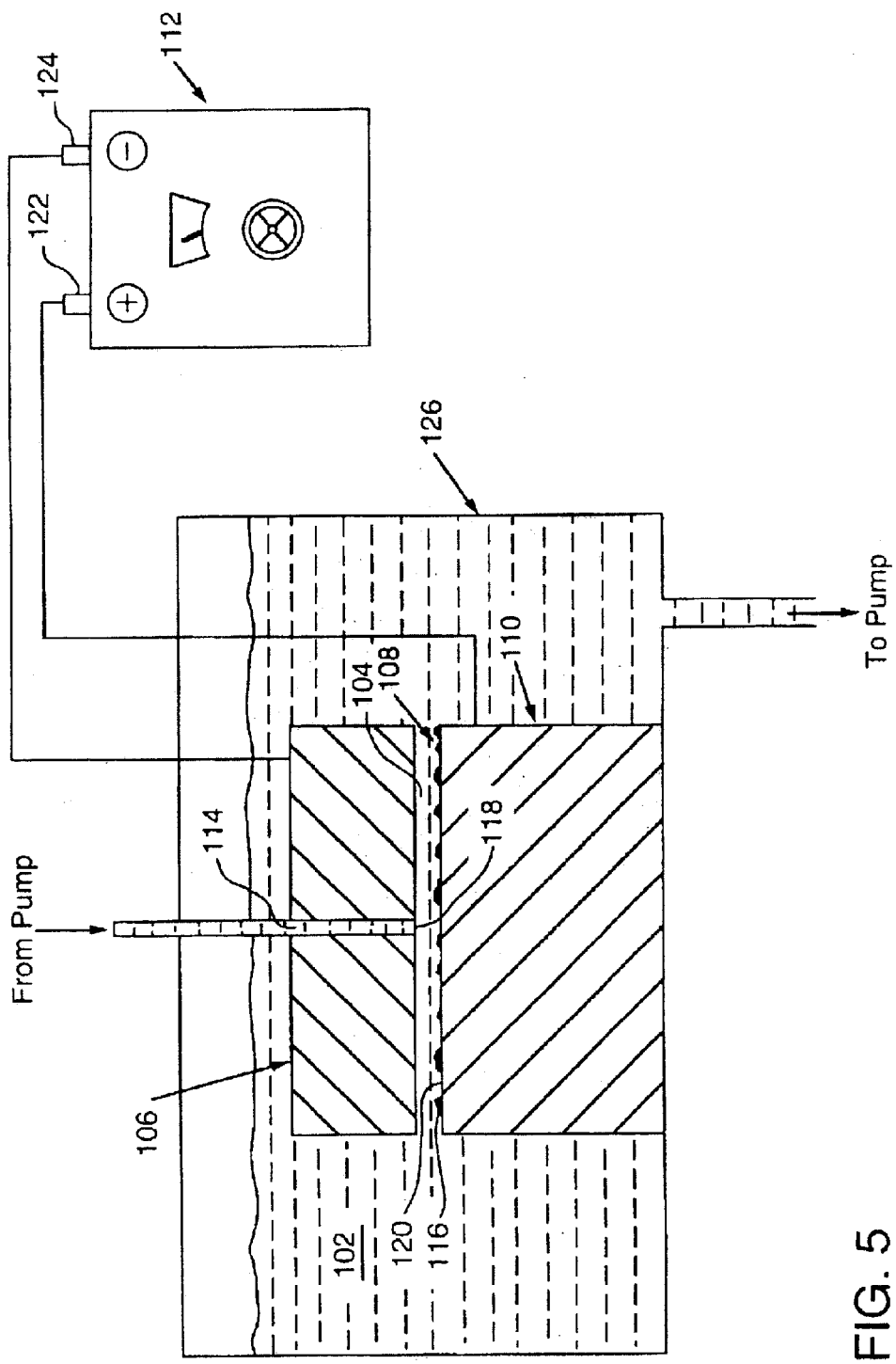
FIG. 5 is a diagrammatic representation, partially in cross section, of the arrangement of the elements of a typical electrochemical etching process.

FIG. 5 diagrammically shows the arrangement of the elements of a typical electrochemical etching process. After the maskant material has been applied and cured, the exposed portion 120 of the attachment surface 108 of workpiece 110 is ready to be electrochemically etched. The exposed portion 120 of the attachment surface 108 is that portion of the attachment surface 108 which is not covered by maskant deposits 116. A tank 126 may be used to submerge the tooling 106 and the workpiece 110 under an electrolyte fluid 102. The electrolyte fluid 102 fills the work gap 104 between the tooling 106 and the attachment surface 108 of the workpiece 110. The electrolyte fluid 102 is pumped at controlled rate through a passageway 114 in the tooling 106 and out through an orifice 118 into the work gap 104. The tooling 106 is in electrical connection with the negative terminal 124 of a direct current power supply 112 and thus becomes the cathode of the electrochemical etching process. The workpiece 110 is in electrical connection with the positive terminal 122 of the same direct current power supply 112 and thus becomes the anode of the electrochemical etching process.

The electrolyte fluid 102 for electrochemically etching a cobalt-chromium alloy is preferably a solution containing the proportions of one pound each of NaCl and NaNO.sub.3 dissolved in one gallon of water. One skilled in the art of electrochemically etching metals will recognize and employ the appropriate electrolyte fluid 102 to be used for the type of metal of a particular workpiece 110. Control of the flow rate of the electrolyte fluid 102 through the work gap 104 is important because the electrolyte fluid 104 must adequately remove both the heat and the reaction products of the electrochemical process. The optimum flow rate level is related to the amount of current employed. Higher ratios of flow rate to current give better removal of heat and reaction products. For the electrochemical etching a cobalt-chromium alloy, for example, the electrolyte fluid 102 should flow through the work gap 104 at a rate of about 0.15–0.5 gallons per minute per 100 amps and have a temperature of between about 100–130.degree. F. One skilled in the art of electrochemically etching metals will be able to determine the proper values of these parameters to use with a particular application.

The tooling 106 may be made from any material suitable for use in electrochemical etching such as copper, nickel, or an alloy of tungsten-copper. The tooling 106 should be configured so that the work gap 104 between the tooling 106 and the attachment surface 108 is substantially uniform. This is accomplished by making the tooling 106 substantially conformal to the attachment surface 108. Preferably, the work gap 104 is between about 0.020–0.250 inches, more particularly between about 0.060–0.120 inches. One skilled in the art of electrochemically etching metal will be able to determine the proper work gap 104 to use for a particular application. A direct current voltage difference between the tooling 106 and the attachment surface 108 of between about 8V–24V and a specific amperage of at least about 50 amps per square inch of exposed portion 120 of the attachment surface 108 are to be maintained during the electrochemical etching of a cobalt-chromium workpiece 110. Preferably, the direct current voltage difference between the tooling 106 and the attachment surface 108 is between about 12–18V and the specific amperage is about 75–120 amps per square inch of exposed portion 120 of the attachment surface 108. The values of these parameters for use with other materials are readily determinable by one skilled in the art of electrochemical etching metals. The stated conditions will produce a metal removal rate of about 0.003 inch per minute when the workpiece 110 material is a cobalt-chromium alloy.

Referring now to the second illustration of FIG. 1, the electrochemically etched result is illustrated, based on the applied maskant shown in the upper illustration. The unfinished surface indication line 24, shown as a chain, indicates the original level identified by the letter A at which the surface began. The first electrochemically etched surface 25 identified by the letter B shows the resultant electrochemically etched surface. The electrochemical etching is continued until a desired etch depth of about 0.001–0.010 inch is achieved. Preferably, the etching is continued until a desired etch depth of about 0.002–0.007 inches is achieved. The time period and other parameters of the electrochemical etching process, particular the specific amperage, may be adjusted upwardly or downwardly to achieve a heavier or lighter etching. The electrochemical etching process is halted by removing the voltage difference between the tooling 106 and the workpiece 110.

The maskant material on the attachment surface 106 is removed after each electrochemical etching step. The maskant material may be removed in a variety of ways. The maskant material may be removed mechanically or chemically. Depending on the size and number of coated objects, mechanical brushing or blasting of the maskant may peel it off. In the preferred embodiment of the invention using a cobalt-chromium alloy workpiece and the Hysol ER1006 maskant material, the workpiece is immersed in an aqueous solution of an alkaline cleaner to dissolve the maskant material. Preferably, the temperature of the alkaline cleaner solution is between about 80–145.degree. F. The immersion time is about 5 to 10 minutes or until the maskant is removed. Water blasting is employed to remove any clinging maskant material which was softened by the alkaline cleaning solution.

Preferably, the masking/electrochemical etching process is repeated three times, though useful attachment surfaces may be obtained through the use of fewer and more numerous cycles. The amount of material removed during each cycle is to be determined by the particular application. Preferably, substantially the same amount of material, as measured by depth of material removal, is removed in each cycle. When multiple masking/electrochemical etching cycles are employed, it is preferable that the attachment surface 106 be blasted with 80 to 120 mesh alumina grit prior to the application of the maskant material so as to promote the adhesion of the maskant material.

Referring again to the second illustration of FIG. 1, a number of surface features may be identified. A primary plateau 30 corresponds to the applied maskant plateau 15 illustrated in the top drawing. The heavy maskant coat completely protects the device surface, preventing any metallic material from being removed at this point A secondary plateau 35 corresponds to the thin layer 20 illustrated in the above drawing. The intermediate height of the secondary plateau between levels A and B indicates that the maskant performed for some period during the electrochemical etching cycle but failed at an intermediate time allowing some of the alloy to be etched away. A small promontory, third from the left as shown in FIG. 1, also illustrates a small secondary plateau 35. Gradually sloped feature 40 corresponds to a gradually tapering maskant coverage which partially protects the underlying substrate during the electrochemical etching cycle. A highly sloped feature 44 indicates a thicker maskant coating which enjoyed a highly defined perimeter before the electrochemical etching. A medium sloped feature 45 indicates a maskant condition intermediate the two previously described. The extremes of the electrochemical etching are indicated by unetched level 46 and first electrochemically etched level 47 which illustrate the effect of complete maskant coating versus no maskant coating. It should be noted that the base of each surface feature provides full dimensionally filleted radii.

FIG. 2 also employs two illustrations to display the effects of a second masking/electrochemical etching cycle. The upper illustration corresponds to the second illustration of FIG. 1, the lowest extreme being found at the level indicated as B. The maskant is again applied to a clean and prepared surface in a random fashion according to the same techniques described with reference to FIG. 1. As before, a randomized pattern is preferable in which a wide variety of maskant surface features is achieved. Second applied maskant points 50 illustrate a variety of positions in which the maskant may be applied to the now irregular surface features of first electrochemically etched surface 25.

Moving to the second illustration of FIG. 2, the first electrochemically etched surface indication line 55 is shown in chain line to indicate the previous surface prior to the second electrochemical etching cycle. The second electrochemical etching cycle is performed under identical conditions as that described with reference to FIG. 1 to again achieve an approximately 0.001–0.010 inch electrochemical etch. Second electrochemically etched surface 60 is shown at level C, indicating a resultant electrochemically etched surface. As previous described, the number of surface features are illustrated corresponding to the characteristics of the applied maskant. A highly sloped surface feature 44 corresponds again to a sharply defined and relatively thick application of maskant while a gradually sloped surface feature 40 corresponds to a gradually thinning maskant application. This feature is particularly visible in the two illustrations contained in FIG. 2 in which the gradual thinning of the maskant application is particularly exaggerated.

As can be seen in the second illustration of FIG. 2, three major levels of surface features are illustrated with a few intermediate features present to demonstrate the effects of partial maskant failure. A few points remain at unetched level 46 indicating maskant coverage during both electrochemical etching cycles. Some points are illustrated at first electrochemically etched level 47 indicating maskant coverage during one of the two cycles, while points located at second electrochemically etched level 75 have been exposed to the electrochemical etching process during both of the electrochemical etching cycles. The increasing level of complexity of surface forms is apparent with comparison between FIGS. 1 and 2.

FIG. 3 is essentially a repetition of FIG. 2 having an upper illustration showing the application of third applied maskant points 80 to the now highly featured second electrochemically etched surface 60 at level C. The increasing complexity of the surface of the electrochemically etched device contributes also to the complexity of the maskant forms when applied to the irregular surface. The second illustration of FIG. 3 is shown to demonstrate the effect of a less intense electrochemical etching cycle, being roughly one-half of the depth shown in FIGS. 1 and 2. The number and intensity of each electrochemical etching cycle is dependent on the complexity of features required by the application and may be performed in any order. As shown in the second illustration of FIG. 3, a gradually sloped surface feature 40 retains its gradually sloped character from one cycle to the next when not covered by a maskant. This is to illustrate the consistent and uniform attack on the surface by the electrochemical etching process. Highly sloped surface feature 44 again illustrates the effect of a highly stable maskant agglomeration while medium sloped surface feature 45 again demonstrates an intermediate condition. As illustrated in the second drawing of FIG. 3, four major surface levels are illustrated. Points at unetched level 46 are still apparent although fewer in number and relatively rare. A number of plateaus remain at first electrochemically etched level 47 and second electrochemically etched level 75. Those areas which have been exposed during all three electrochemical etch process cycles enjoy depressions at third electrochemically etched surface 100 corresponding to level D in FIG. 3. These levels correspond to areas which have had coverage during all three cycles, two cycles, one cycle and no cycles, respectively. The result, as shown by third electrochemically etched surface 90, is a highly non-uniform featured surface which, compared with its length, also exhibits a large surface area. The different levels of depression and protrusion are particularly adapted to permit the ingrowth of bone and to allow for a firm anchoring of the bone along the surface of an implant structure. The different levels of depression and protrusions are also particular adapted to permit the inflow and anchoring of adhesives.

Figure 6:
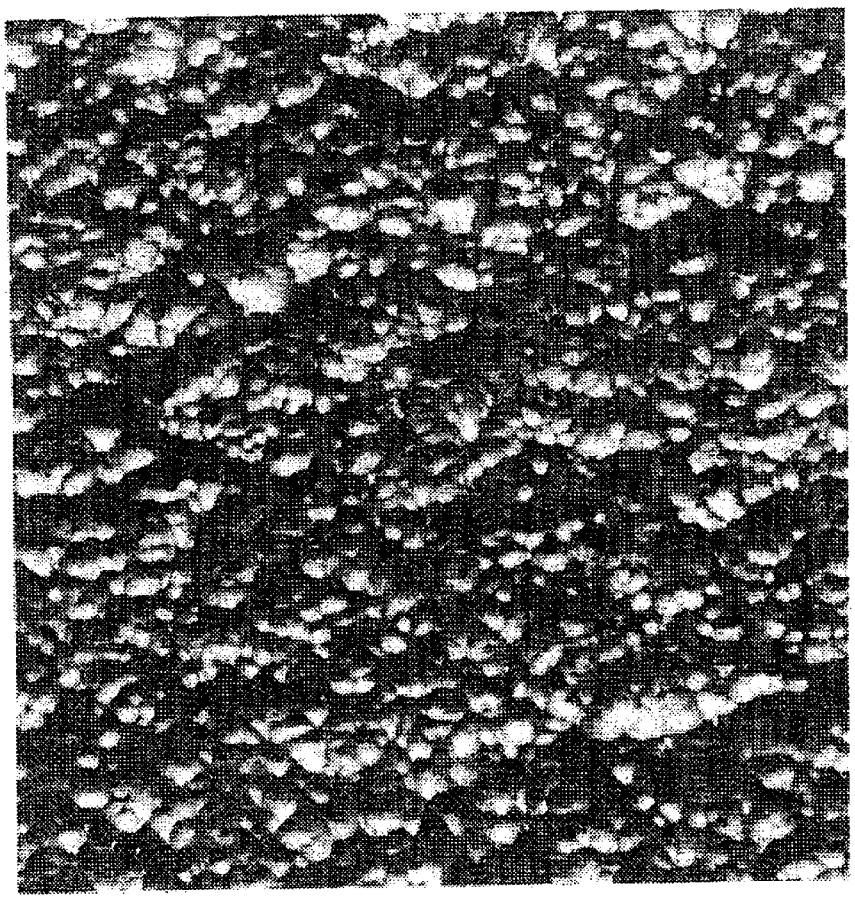
FIG. 6 is a photomicrograph of the electrochemically etched surface.

FIG. 6 illustrates a sample resultant surface. All surface features are fully filleted and irregularly shaped to promote bone ingrowth and the inflow of adhesives.

According to a preferred embodiment of the present invention, a method is provided for providing an unfinished surface 1, as described in connection with FIGS. 1 through 6, with an enhanced surface texture having a plurality of micro-features that promote bone ingrowth or osseointegration. According to the method, surface 1 is first subjected to a predetermined number of masking and chemical or electrochemical etching steps as shown and described in conjunction with FIGS. 1 through 6. Depending on the number of masking and chemical or electrochemical etching steps that are performed, a surface texture such as shown in FIG. 1, 2 or 3 will result. After completion of these steps, the resulting surface is then subjected to a blasting step in which a blast media is impinged upon the surface. The blasting step may be performed in conjunction with any known equipment typically used for blasting, including, but not limited to, a blast cabinet having an air gun or nozzle, a wheel abrader machine, or gas jet shot equipment that sputters the blast media in the direction of the part to be treated. One or more of the following five variables will, depending on the type of equipment being used, affect the surface texture produced and that must be taken into consideration during this blasting step: (1) the particular blast media chosen and the grit size thereof; (2) the duration of the blast; (3) the pressure of the blast stream; (4) the distance between the source of the blast media, such as a nozzle, and the surface being treated; and (5) the angle at which the source of the blast media, and thus the stream of the blast media, is directed toward the surface being treated. One preferred embodiment incorporates blast media of any metallic material that can be dissolved or otherwise removed without damage to the substrate material. One preferred solvent is nitric acid, which may be utilized to dissolve materials such as steel, aluminum or copper.

Preferably, the blast media is a fractured or split shot media having a grit range of G10 to G120. Acceptable blasting durations are in the range of 1 to 30 seconds, acceptable blasting pressures are in the range of 20 to 120 psi, acceptable distances from the source may be as large as 10 or 12 inches, and acceptable incident angles range from 5 to 90 degrees, with 90 degrees being the angle at which the source of blast media is pointed directly at the surface. As will be appreciated by those of skill in the art, the most suitable values for each of these parameters will vary depending on the particular type of material making up surface 1 and the values chosen for the other parameters. According to one embodiment of the present invention, G40 fractured steel shot is used as the blast media in a blast cabinet for a duration of 5 to 15 seconds, most preferably 2 to 6 seconds, at a pressure of approximately 80 psi, at a distance of 2 to 4 inches and an incident angle of 40 to 50 degrees. According to a most preferred embodiment, this preferred blasting step is performed after the surface has been masked and chemically or electrochemically etched as described herein three times, removing 0.005" of material in the unmasked areas during each etching step.

After the blasting step, the surface is subjected to a cold flash step to remove stains in which the surface is immersed in a hydrofluoric acid/nitric acid bath for at least the minimum amount of time required to ensure a bright, stain free surface. Preferably, the hydrofluoric acid/nitric acid bath is maintained at room temperature and consists of the following per 100 gallon solution: 11 gallons nitric acid 42 Degrees Baume, 6.5 gallons hydrofluoric acid 70%, 4 pounds titanium (CP), balance deionized water. In addition, the cold flash step preferably removes no more than 0.0002 inches of material from the surface by controlling the time in which the surface is immersed in the bath. Any special areas of the surface, such as threaded holes or trunnions, may be plugged or covered to prevent damage thereto.

As will be further appreciated by those of skill in the art, the blasting step will result in the surface being contaminated with embedded blast media particulate debris. According to the method of the present invention, this embedded particulate debris is removed during a debris removal step, which in the above embodiment is a nitric acid passivation step. Those skilled in the art will appreciate that in alternative embodiments, the solvent is intended to be matched to the blast media such that the blast media embedded in the substrate is completely removed by the solvent without deleterious effect on the substrate. The debris removal step preferably follows the cold flash step, in which the surface is immersed in a nitric acid bath that leaches the embedded steel particulate debris from the surface. According to a preferred embodiment, the nitric acid bath consists of nitric acid, 40% by volume, in deionized water, and the surface is immersed for no less than 6 hours. Also, the nitric acid bath is preferably maintained at room temperature at a specific gravity between 1.175 and 1.225 (60°/60°). The surface is then rinsed in deionized water and air-dried.

Figure 7:
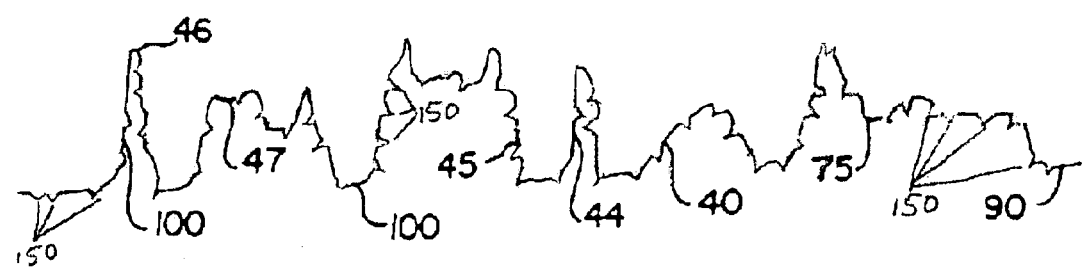
FIG. 7 is a diagrammatic representation of surface shown in FIG. 3 following the blasting, cold flash and debris removal steps of the present invention.
Figure 8:
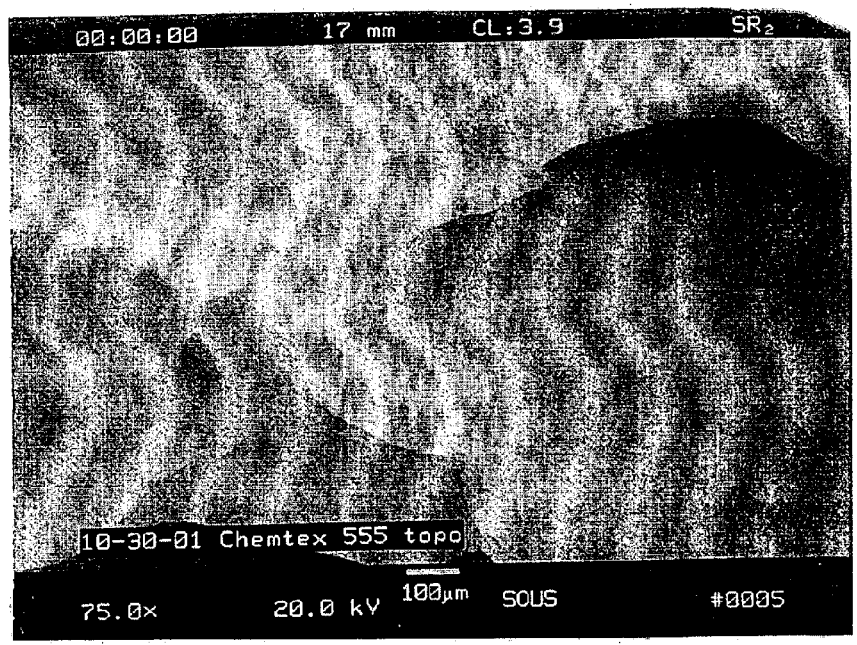
FIG. 8 is a photomicrograph of a surface that has been prepared as shown in FIG. 3.
Figure 9:
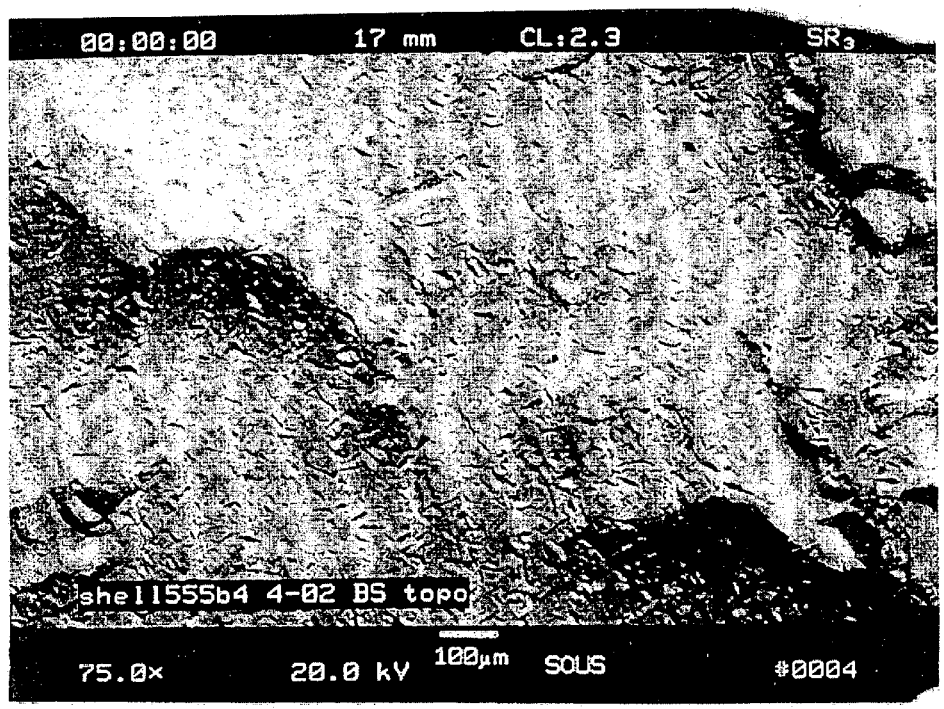
FIG. 9 is a photomicrograph of the surface shown in FIG. 8 following the blasting, cold flash and debris removal steps of the present invention.

Performing the blasting and passivation steps according to the present invention on the surface shown in FIG. 3 will result in a surface such as that shown in FIG. 7 that includes a plurality of micro-features 150 comprising recesses or indents that promote greater osseointegration. FIG. 8 is a photomicrograph of a titanium surface that has been masked and chemically etched as described herein three times, removing approximately 0.005 inches of material in the unmasked areas during each etching step. FIG. 9 is a photomicrograph of the same surface after the preferred blasting, cold flash and passivation steps described herein have been performed.

Although particular embodiments of the present invention have been illustrated in the accompanying drawings and described in the foregoing detailed description, it is to be further understood that the present invention is not to be limited to just the embodiments disclosed, but that they are capable of numerous rearrangements, modifications and substitutions.

What is claimed is:

1. An irregular exterior surface portion integral to a substrate material which is particularly adapted to be joined to a second material, the surface portion to be so joined comprising a plurality of randomly sized and spaced protrusions having micro-features located upon said surface portion, produced by the method comprising the steps of:
    a) masking said surface portion of said substrate material in a random pattern with a maskant material, such that less than the entire surface portion is covered thereby;
    b) etching said surface portion such that said substrate material is removed thereby in areas uncovered by said maskant material, and areas covered by said maskant material are left intact;
    c) removing said maskant material;
    d) repeating said masking, etching and maskant removing steps upon said surface portion until a desired surface irregularity is achieved;
    e) blasting the etched surface portion with a blast media to create said micro-features that is dissolvable in a solvent, said blasting resulting in blast media particulate debris being affixed to said surface portion; and
    f) removing said blast media particulate debris affixed to said surface portion during said blasting step using said solvent without substantial deleterious effect upon said substrate material.

2. An irregular exterior surface portion, produced by the method described in claim 1, said step of removing said blast media particulate debris comprising exposing said surface portion to a nitric acid solvent.

3. An irregular exterior surface portion, produced by the method as described in claim 1, wherein said masking, etching and maskant removing steps are repeated two additional times prior to said blasting step.

4. An irregular exterior surface portion, produced by the method as described in claim 3, wherein each of said etching steps removes approximately 0.005 inches of said surface portion.

5. An irregular exterior surface portion, produced by the method as described in claim 1, wherein said blast media comprises a fractured shot blast media.

6. An irregular exterior surface portion, produced by the method as described in claim 5, wherein said blast material is fractured metallic shot.

7. An irregular exterior surface portion, produced by the method as described in claim 6, wherein said blast material is comprised of steel.

8. An irregular exterior surface portion, produced by the method as described in claim 7, wherein said blast material is fractured steel shot.

9. An irregular exterior surface portion, produced by the method as described in claim 1, wherein said blast material has a grit rating between G10 and G120.

10. An irregular exterior surface portion, produced by the method as described in claim 9, wherein said blast material has a grit rating of G40.

11. An irregular exterior surface portion, produced by the method as described in claim 1, wherein said blasting step lasts for between 1 and 30 seconds.

12. An irregular exterior surface portion, produced by the method as described in claim 1, wherein said blasting step utilizes a blasting pressure in the range of 20 to 120 psi.

13. An irregular exterior surface portion, produced by the method as described in claim 1, wherein during said blasting step, a distance between a source of said blast media and said surface portion is less than twelve inches.

14. An irregular exterior surface portion, produced by the method as described in claim 1, wherein during said blasting step a stream of said blast media is directed toward said surface portion at an incident angle of between 5 and 90 degrees.

15. An irregular exterior surface portion, produced by the method as described in claim 1, wherein said blast media comprises a fractured shot blast media, wherein said blasting step lasts for between 1 and 30 seconds, wherein said blasting step utilizes a blasting pressure in the range of 20 to 120 psi, wherein during said blasting step, a distance between a source of said blast media and said surface portion is less than twelve inches and a stream of said blast media is directed toward said surface portion at an incident angle of between 5 and 90 degrees.

16. An irregular exterior surface portion, produced by the method as described in claim 15, further comprising repeating said masking, etching and maskant removing steps upon said surface portion until a desired surface irregularity is achieved prior to said blasting step.

17. An irregular exterior surface portion, produced by the method as described in claim 16, wherein said masking, etching and maskant removing steps are repeated two additional times prior to said blasting step.

18. An irregular exterior surface portion, produced by the method as described in claim 17, wherein each of said etching steps removes approximately 0.005 inches of said surface portion.

19. An irregular exterior surface portion, produced by the method as described in claim 15, wherein said blast media is G40 fractured steel shot.

20. An irregular exterior surface portion, produced by the method as described in claim 15, wherein said blasting step lasts for between 2 and 6 seconds, wherein said blasting step utilizes a blasting pressure of approximately 80 psi, and wherein during said blasting step, said distance between said source of said blast media and said surface portion is between 2 and 4 inches and said stream of said blast media is directed toward said surface portion at an incident angle of between 40 and 50 degrees.

21. An irregular exterior surface portion, produced by the method as described in claim 20, further comprising repeating said masking, etching and maskant removing steps upon said surface portion until a desired surface irregularity is achieved prior to said blasting step.

22. An irregular exterior surface portion, produced by the method as described in claim 21, wherein said masking, etching and maskant removing steps are repeated two additional times prior to said blasting step.

23. An irregular exterior surface portion, produced by the method as described in claim 22, wherein each of said etching steps removes approximately 0.005 inches of said surface portion.

24. An irregular exterior surface portion, produced by the method as described in claim 20, wherein said blast media is G40 fractured steel shot.

25. An irregular exterior surface portion, produced by the method as described in claim 2, wherein said solvent comprises 40% nitric acid, by volume, in deionized water.

26. An irregular exterior surface portion, produced by the method as described in claim 25, wherein said solvent is maintained at room temperature at a specific gravity between 1.175 and 1.225 (60°/60°).

27. An irregular exterior surface portion, produced by the method as described in claim 2, wherein said debris removal lasts for at least six hours.

28. An irregular exterior surface portion, produced by the method as described in claim 1, further comprising the step of exposing said surface portion to a hydrofluoric acid/nitric acid bath before said step of removing said blast media particulate debris.

29. An irregular exterior surface portion, produced by the method as described in claim 28, wherein said hydrofluoric acid/nitric acid bath is maintained at room temperature and consists of 11 gallons nitric acid 42 Degrees Baume, 6.5 gallons hydrofluoric acid 70%, 4 pounds titanium (CP), balance deionized water per 100 gallons thereof.

30. An irregular exterior surface portion, produced by the method as described in claim 2, wherein said blast media comprises a G40 fractured steel shot, wherein said blasting step lasts for between 2 and 6 seconds, wherein said blasting step utilizes a blasting pressure of approximately 80 psi, wherein during said blasting step, a distance between a source of said blast media and said surface portion is between 2 and 4 inches and a stream of said blast media is directed toward said surface portion at an incident angle of between 40 and 50 degrees, wherein said masking, etching and maskant removing steps are repeated two additional times prior to said blasting step, each of said etching steps removing approximately 0.005 inches of said surface portion, and wherein said solvent comprises 40% nitric acid, by volume, in deionized water.

31. An irregular exterior surface portion, produced by the method as described in claim 30, further comprising the step of exposing said surface portion to a hydrofluoric acid/nitric acid bath before said step of removing said blast media particulate debris, said hydrofluoric acid/nitric acid bath being maintained at room temperature and comprising 11 gallons nitric acid 42 Degrees Baume, 6.5 gallons hydrofluoric acid 70%, 4 pounds titanium (CP), balance deionized water per 100 gallons thereof.

* * * * *